(12) United States Patent
Muller (10) Patent No.: US 10,835,742 B2
(45) Date of Patent: Nov. 17, 2020

(54) SEGMENTED FLAT ELECTRODE (71) Applicant: BERLIN HEALS HOLDING AG, Zurich (CH)

(72) Inventor: Johannes Muller, Berlin (DE)

(73) Assignee: BERLIN HEALS HOLDING AG, Zurich (CH)

( * ) Notice: Subject to any disclaimer, the term of this patent is extended or adjusted under 35 U.S.C. 154(b) by 74 days.

(21) Appl. No.: 15/500,546

(22) PCT Filed: Jul. 31, 2015

(86) PCT No.: PCT/EP2015/067698
§ 371 (c)(1),
(2) Date: Jan. 31, 2017

(87) PCT Pub. No.: WO2016/016438
PCT Pub. Date: Feb. 4, 2016

(65) Prior Publication Data
US 2017/0216582 A1    Aug. 3, 2017

(30) Foreign Application Priority Data
Jul. 31, 2014   (EP) .................................... 14179231

(51) Int. Cl.
*A61N 1/05* (2006.01)
*A61N 1/00* (2006.01)

(52) U.S. Cl.
CPC ............. *A61N 1/0597* (2013.01); *A61N 1/00* (2013.01); *A61N 1/05* (2013.01); *A61N 1/056* (2013.01);
(Continued)

(58) Field of Classification Search
CPC ......................... A61N 1/0597; A61N 1/0492
See application file for complete search history.

(56) References Cited

U.S. PATENT DOCUMENTS 6,330,466 B1 * 12/2001 Hofmann ............ A61B 5/04001
600/378
7,640,065 B1   12/2009 Kroll
(Continued)

FOREIGN PATENT DOCUMENTS

CN   101522257 A   9/2009
CN   103170059 A   6/2013
(Continued)

OTHER PUBLICATIONS

International Preliminary Report on Patentability issued from the International Bureau in counterpart International Application No. PCT/EP2015/067698, dated Jan. 31, 2017.
(Continued)

*Primary Examiner* — Alyssa M Alter
(74) *Attorney, Agent, or Firm* — Sughrue Mion, PLLC (57) ABSTRACT

An electrode (10) for treating organic tissue by means of direct current, comprising an electrode holder (20), at least one electrically conductive electrode surface (30), which is let into the electrode holder (20), wherein the at least one electrode surface (30) is connected to at least one control element (400) and wherein the at least one control element (400) is connected to a control and energy supply unit by way of electrical lines (60, 70), wherein the at least one control element (400) is configured in such a way that each individual electrode surface (30) is actuable by the at least one control element (400) in such a way that a current density (J) provided within a predetermined interval for each one of the at least one electrode surfaces (30) can be maintained or that a current density (J) for each one of the at least one electrode surfaces (30) can be maintained around a predetermined value.

16 Claims, 5 Drawing Sheets

(52) U.S. Cl.
CPC ......... *A61N 1/0565* (2013.01); *A61N 1/0587* (2013.01)

(56) References Cited

U.S. PATENT DOCUMENTS

2009/0209840 A1 8/2009 Axelgaard
2010/0152864 A1 6/2010 Isaacson et al.

FOREIGN PATENT DOCUMENTS

WO 2006/106132 A1 10/2006
WO 2007/070579 A2 6/2007

OTHER PUBLICATIONS

Communication dated Jun. 29, 2018 issued by the State Intellectual Property Office of People's Republic of China in counterpart application No. 2015800418272.
International Search Report of PCT/EP2015/067698 dated Oct. 19, 2015.

* cited by examiner

SEGMENTED FLAT ELECTRODE

CROSS REFERENCE TO RELATED APPLICATIONS

This application is a National Stage of International Application No. PCT/EP2015/067698 filed Jul. 31, 2015, claiming priority based on European Patent Application No. 14 179 231.7, filed Jul. 31, 2014, the contents of all of which are incorporated herein by reference in their entirety.

TECHNICAL FIELD

The present invention relates to an electrode and to a method for treating organic tissue by means of direct current.

PRIOR ART

WO 2006/106132 A1 describes an electrode for treating organic tissue by means of direct current.

US 2010/152864 A1 describes an implant for use on a bone, comprising an electrical stimulation system, in which the control is suitable for limiting or controlling the current density at the implant-bone interface.

WO 2007/070579 A2 describes an implant for stimulating the regeneration of damaged spinal nerves, in which a direct current is applied near the damaged sites at a level sufficient to induce regeneration, without applying a current level at which tissue toxicity occurs.

PRESENTATION OF THE INVENTION

A problem addressed by the present invention is therefore that of improving the effect of the treatment while simultaneously increasing the safety of the treatment.

This problem is solved according to the invention by electrodes having the features of claim 1 and by a method having the features of claim 14.

The electrode according to the invention for treating organic tissue by means of direct current comprises an electrode support and at least one electrically conductive electrode surface which is embedded in the electrode support, wherein the at least one electrode surface is connected to at least one control element and wherein the at least one control element is connected to a control and power supply unit by way of electric lines.

The at least one control element is configured in such a way that each individual electrode surface is controllable by the at least one control element in such a way that a current density provided within a predetermined interval for each one of the at least one electrode surface can be maintained, or that a current density for each one of the at least one electrode surface can be maintained around a predetermined value.

Preferably, the at least one control element is situated on the back or at the side of the at least one electrode surface.

The predetermined current density on the electrode can be maintained by controlling/regulating the current or the voltage. The current density can be maintained, in particular, for a time period of several minutes up to half an hour. Subsequently, a direct current having the opposite polarity can be provided for the same time period or for a shorter or longer time period; this makes it possible to reliably prevent electrolytic residue from forming due to the current introduction.

As a result of maintaining a previously set current density, it can be ensured that the current density becomes neither too high nor too low. A current density which is too high can be harmful to the organic tissue, and a current density which is too low can have a diminished therapeutic effect.

Preferably, the organic tissue is cardiac tissue, preferably a heart muscle. The electrode according to the invention is situated directly at the heart muscle, the so-called epicardium, so that a conductive connection results between the heart muscle and the electrode.

In one preferred embodiment, the at least one control element comprises a first control element which is designed as a constant-current source, and a second control element which establishes the voltage and the polarity at the constant-current sources.

Preferably, at least one first control element is assigned to each individual electrode surface. This permits a precise control/regulation of each individual electrode, which results in a more precise maintenance of the predetermined value.

Preferably, at least one second control element is assigned to all electrode surfaces jointly. The first control element is connected to the second control element by way of electric lines, wherein the second control element is advantageously situated at a distance from the at least one electrode surface. The second control element is situated close to the electrode, however, for example, in a connection area of the electrode having a supply line which includes the electric lines for controlling/regulating the current density and, optionally, further electric lines, such as, for example, a measuring line, by means of which, e.g., an EKG or an impedance can be measured, or a further control/regulating line.

The second control element is situated upstream from the first control element and performs higher-order functions. For example, the current or voltage for the second control element is predetermined and the first control element operates with this predetermined operating current or this predetermined operating voltage. This structure of the first and the second control elements allows for a compact design of the individual control elements and simplifies the control/regulation of the particular current density at the particular electrode.

In one advantageous embodiment, at least two electrode surfaces are embedded in one shared electrode support. The electrode support is designed so as to be integrally interconnected. Due to this arrangement of the electrode surfaces, an electrode element can be implemented, which is easy to handle and has sufficient flexibility, so that the electrode can follow the movements of the organic tissue, and a detachment of the electrode from the surface of the organic tissue can be reduced or avoided.

In yet another advantageous embodiment, each of the at least two electrode surfaces, with the corresponding at least one control element, is embedded in a separate electrode support, wherein these individual electrode supports are connected to one another by means of a connection strand. An electrode designed in this way is distinguished by high flexibility. This flexibility ensures that the electrode does not detach from the surface of the organic tissue due to the movements thereof.

Further embodiments comprising uniformly distributed electrode surfaces of the same size are likewise possible, for example, a circular or elliptical electrode having electrode surfaces which have the shape of a circular segment or an elliptical segment, or an annular electrode having electrode surfaces in the shape of annular segments.

The number of electrode surfaces can be two to two hundred, preferably ten to one hundred. The following applies: The greater the number of electrode surfaces, i.e., the smaller the segmenting, the less likely it is that the electrode will become detached. It is likewise possible that the detachment of one single electrode surface is less significant in the case of smaller segmenting, which has an advantageous effect on the treatment.

The electrode can be segmented into an even or uneven number of electrode surfaces. Alternatively, multiple rows of electrode surfaces can be situated laterally with respect to the longitudinal central axis. Circular, annular, or elliptical electrodes can likewise comprise multiple rows of concentrically situated electrode segments.

Embodiments having electrode surfaces which are non-uniformly distributed and/or are not the same size are likewise possible. Areas of the electrode having smaller electrode surfaces allow for a larger curvature. Electrodes can be designed in such a way that the distribution and arrangement of the electrode surfaces are adapted to the curvatures prevailing on the surface of the heart. For example, one electrode comprises smaller electrode surfaces, which are laterally surrounded by larger electrode surfaces, along its longitudinal central axis. Alternatively, one electrode can comprise larger electrode surfaces in its central area and smaller electrode surfaces in its edge area.

The electrode surfaces can be produced from thin, conductive, biocompatible materials having low polarization, for example from platinum or platinum iridium. Alternatively, the electrode surfaces can be a knitted fabric or woven fabric produced from thin, conductive, biocompatible materials having low polarization, for example from platinum or platinum iridium.

The knitted-fabric or woven-fabric structure has the advantage that it can adapt very well to the underlying tissue. Such structures likewise have a certain permeability for fluids, which at least partially prevents an accumulation of fluids between the underlying tissue and the electrode surface.

The knitted-fabric or woven-fabric structure promotes an at least partial adhesion with the underlying tissue, for example, with connective tissue, which improves the contact between the underlying tissue and the electrode.

The knitted fabrics or the woven fabrics can be embedded in one single electrode support, in each case, or in one shared electrode support.

Alternatively, the knitted fabric or the woven fabric can have alternating conductive and non-conductive areas, so that individual electrode surfaces, which are independent of one another, form an interconnected knitted fabric or woven fabric.

The individual knitted-fabric or woven-fabric surfaces can be enclosed by an electrically conductive frame. Such a frame prevents the knitted fabric or woven fabric from falling apart as a result of movement. The stiffness of the frame can be influenced by the dimensions and material properties of the frame. Alternatively, the frame can also be produced from a non-conductive material.

In the method according to the invention for controlling the current density (J) on an electrode according to the invention, the voltage applied at each electrode is controlled/regulated in such a way that a current density predetermined for each individual electrode surface is maintained.

Preferably, the control/regulation is implemented by a MOSFET element or a bipolar transistor. These electrical components are distinguished by a compact design and ensure a reliable and exact control/regulation.

In yet another embodiment, the electrode comprises at least one one-way valve which permits the drainage of fluid which accumulates under the electrode. Draining the fluid makes it possible to prevent the electrode from gradually detaching from organic tissue or it simplifies detachment. Consistently good contact between the electrode and the surface of the organic tissue is therefore ensured.

Preferably, the at least one one-way valve is situated within an electrode surface. As a result, the fluid is drained at the point where it has the greatest negative influence on the contact between the electrode surface and the surface of the organic tissue.

In yet another preferred exemplary embodiment, the at least one one-way valve is situated between adjacent electrode surfaces. The arrangement between adjacent electrode surfaces permits the arrangement of the at least one one-way valve in the electrode support and makes it possible to design the electrode surfaces without openings.

Preferably, the at least one one-way valve is a diaphragm valve having a valve diaphragm.

A method for controlling the current density (J) on an electrode according to the present invention is characterized in that the current (I) flowing through each electrode is regulated in such a way that a current density (J) provided within a predetermined interval for each individual electrode surface is maintained. Alternatively, the current density (J) is maintained around a predetermined value for each one of the at least one electrode surface.

Due to the selection of a current density interval, no adjustments of the presetting of the current density are necessary in this interval.

If the current density is regulated around a predetermined value, a treatment-specific current density can be set, which is particularly advantageous.

Each electrode according to the invention can be used as a current-feeding or current-receiving electrode.

If the control electronics are not provided on the electrode or electrodes, a series of lines would be necessary between the power supply and the electrodes; this is then at least one line per electrode, which, when several electrodes are present, results in an inflexible cable assembly. The invention provides a solution in this case, since the connection to the control and power supply unit is a two-wire connection which is used exclusively to supply current, while the control and regulation takes place by way of the control elements situated in the electrode.

Further embodiments are described in the dependent claims.

BRIEF DESCRIPTION OF THE DRAWINGS

Preferred embodiments of the invention are described in the following with reference to the drawings which are intended merely for the purpose of explanation and are not intended to be interpreted to be limiting. In the drawings.

DESCRIPTION OF PREFERRED EMBODIMENTS

Figure 1:
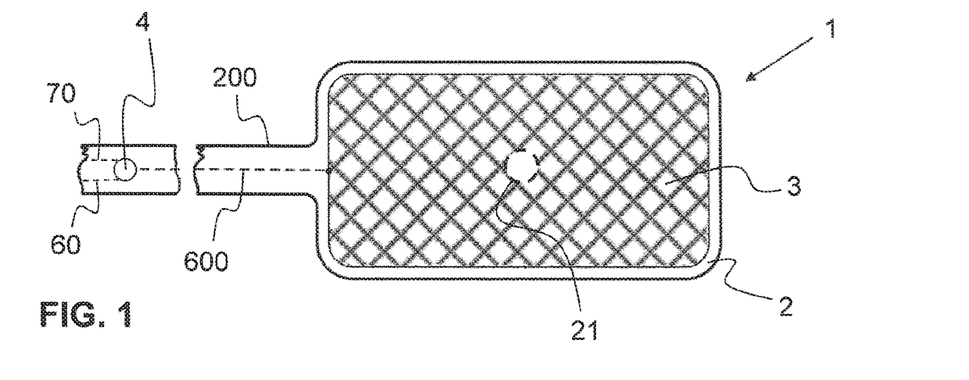
FIG. 1 shows a single electrode according to the invention.

FIG. 1 shows a single electrode 1 according to the invention comprising a first electrode support 2, in which a first electrode surface 3 is embedded. The first electrode support 2 surrounds the first electrode surface around the sides and the back, at least partially, preferably completely. The electrode surface 3 is connected by way of an electric line 600 to a first control element 4 which is situated at a distance from the electrode surface 3 in a supply line 200 and which is connected by way of electric lines 60, 70 to a control and power supply unit 900 depicted in FIG. 10. The first control element 4 can be situated close to the electrode surface 3, i.e., in the connection area having the supply line 200, in the control and power supply unit 900, or therebetween. The current density J of the electrode surface 3 can be controlled/regulated by means of the first control element.

A non-illustrated second control element 5 (see FIG. 5) can be situated together with the first control element 4, adjacent thereto, or in the control and power supply unit 900.

An electrode surface can possibly detach from the tissue on which it preferably completely rests. If the electrode is then regulated in such a way that a constant current I flows therethrough, the current density increases when the electrode becomes detached, since the area through which the current I can flow is reduced.

Given, for example, an electrode surface 3 which is 100 square centimeters in size, and a direct current I of 1 milliampere, the current density is 0.01 milliamperes per square centimeter. If the electrode surface detaches from the tissue, then only 10 square centimeters (i.e., one-tenth), for example, are still in contact, in which current can flow. If constant-current regulation were applied, the current density would increase ten-fold, to 0.1 milliamperes per square centimeter, since the area has become ten times smaller due to the detachment. Such high current densities are undesired, since they can trigger cardiac arrhythmia, for example.

Figure 11:
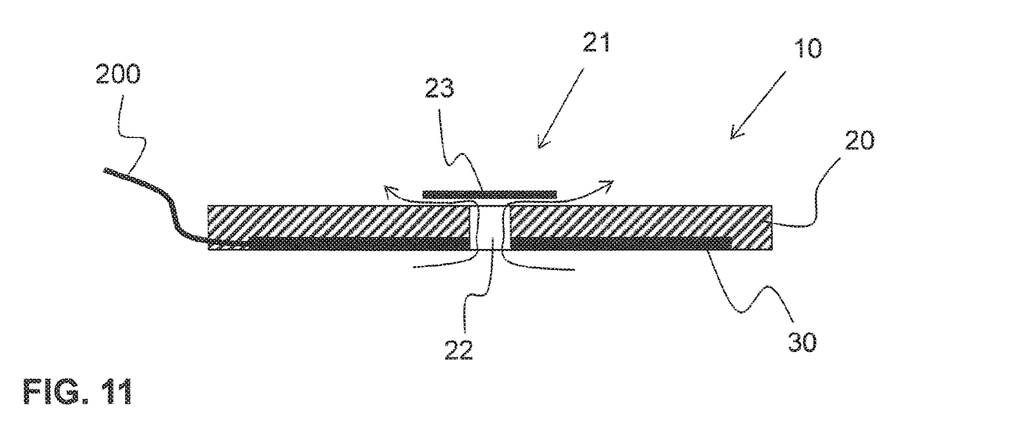
FIG. 11 shows an electrode according to the invention comprising a one-way valve.

The electrode 1 optionally comprises at least one one-way valve 21 which essentially comprises an opening 22 and a diaphragm 23 covering the opening 22 on the outer side. A schematic sectional view of the one-way valve 21 is depicted in FIG. 11. The diaphragm is made from silicone, for example. The at least one one-way valve 21 is situated within the electrode surface 3.

Figure 2:
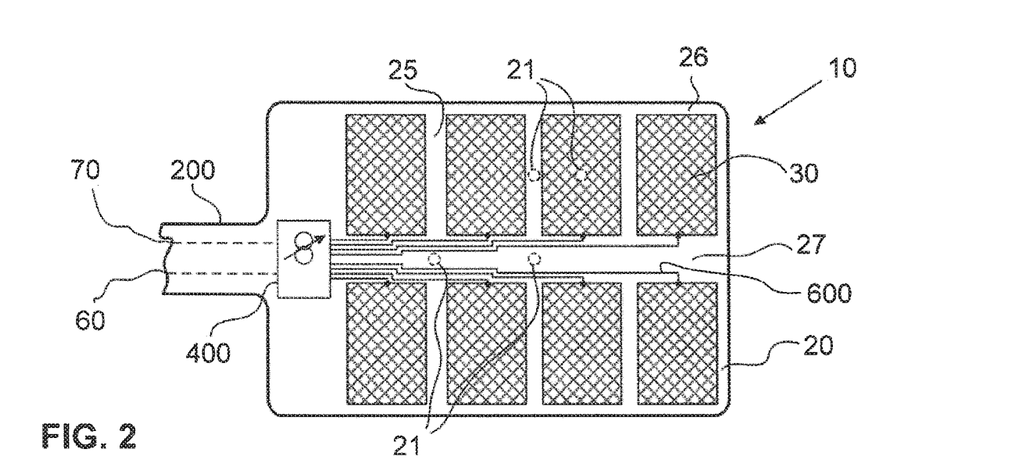
FIG. 2 shows a further embodiment of an electrode according to the invention.

FIG. 2 shows yet another embodiment of a segmented electrode 10 according to the invention. The electrode 10 comprises multiple electrode surfaces 30 which are separated from one another and are embedded in a shared, second electrode support 20.

All electrode surfaces 30 are of the same size and are situated in pairs, symmetrically with respect to the longitudinal central axis of the electrode. Eight electrode surfaces 30 are shown, wherein four are situated on one side of the longitudinal central axis and four are situated on the opposite side of the longitudinal central axis.

The electrode support 20 comprises a border 26 which laterally encloses all electrode surfaces and comprises webs 25 which separate the individual electrode surfaces from each other, wherein the web lying on the longitudinal central axis is a central web 27 which contains the electric lines 600 which connect a control module 400 to the individual electrode surfaces 30. The control module 400 comprises multiple control elements 4 which control/regulate the current density J in the particular electrode surface. The number of control elements 4 per control module 400 correlates with the number of electrode surfaces 30.

Electric lines 60, 70 connect the control module 400 to the non-illustrated control and power supply unit 900. The second control element 5 (not shown) can be disposed in the control module 400, adjacent thereto, or in the control and power supply unit 900. In other words, situated between the control and power supply unit 900 and the control module 400 are electric lines 60, 70, in particular, which are used for the power supply and can establish the connection to the battery provided there.

In the depicted arrangement, the electrode surfaces 30 are situated opposite one another with respect to the longitudinal central axis of the electrode 10 in groups of two and form one pair of electrode surfaces in each case. Four such pairs are situated next to one another in the direction of the longitudinal central axis.

The use of a plurality of electrode surfaces 30 has the advantage that, if one of the electrode surfaces 30 becomes detached, the current density J of the corresponding electrode surface can be regulated in such a way that it does not exceed an established value and the remaining electrode surfaces 30 of the segmented electrode 10 are not adversely affected thereby.

The electrode 10 comprises at least one one-way valve 21. The at least one one-way valve 21 can be situated within the webs 25. Alternatively or additionally, said valve can be situated within an electrode surface 30. Alternatively or additionally, said valve can be situated within the central web 27.

Alternatively or additionally, said valve can also be situated in the middle of four adjoining electrode surfaces 30, i.e., at intersections of the webs 25 and the central web 27. The at least one one-way valve 21 is designed in such a way that fluid which accumulates under the electrode surface 30 can reach the back side of the electrode 10 in only one direction through said electrode.

Figure 3:
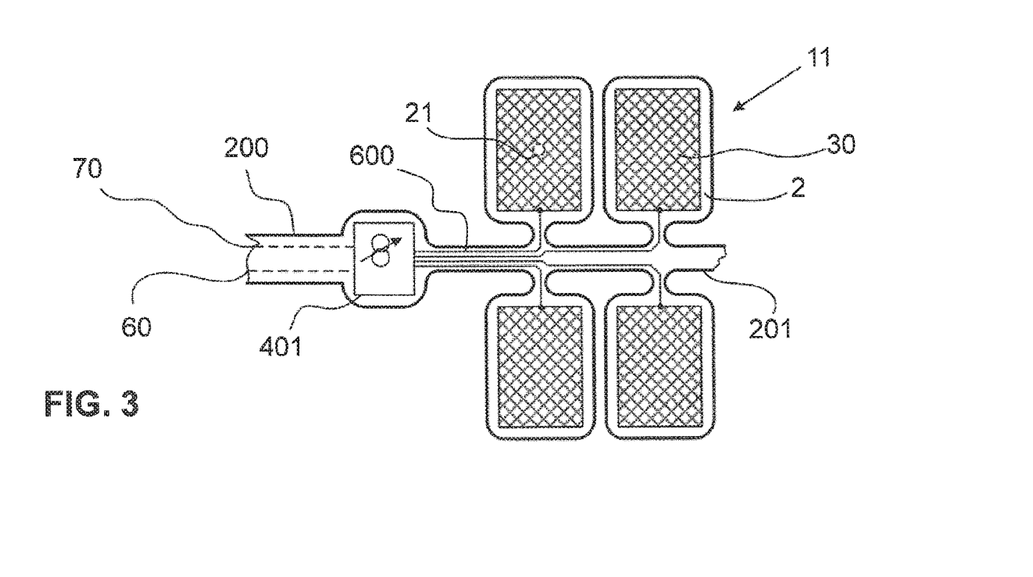
FIG. 3 shows a further embodiment of an electrode according to the invention.

FIG. 3 shows one alternative embodiment of a segmented electrode 11 according to the invention. In contrast to the previous embodiment, each of the individual electrode areas 30 is embedded in separate electrode supports 2 which are connected to one another by means of a connection strand 201.

As in the previous embodiment, a control module 400 is provided, by means of which the current density J of each electrode area 30 can be controlled/regulated. In turn, the control module 400 is connected to the non-illustrated control and power supply unit by way of electric lines 60, 70 which are routed in the supply line 200.

Electric lines 600 extend from the control module 400 to the particular electrode surface 30. The electric lines 600 are routed in the connection strand 201. The connection strand comprises lateral branches along its longitudinal direction, each one of which leads to an electrode surface 30.

The electrode 10 can comprise at least one one-way valve 21 which is situated within an electrode surface 30.

In the case of the electrode surfaces 3, the electrodes 1, 10, 11 depicted in FIGS. 1 to 3 are knitted fabrics or woven fabrics made of thin, conductive, biocompatible metal wires having low polarization, for example, of platinum or platinum iridium. Alternatively, thin metal foils can be used instead of the knitted fabrics or woven fabrics.

Figure 4:
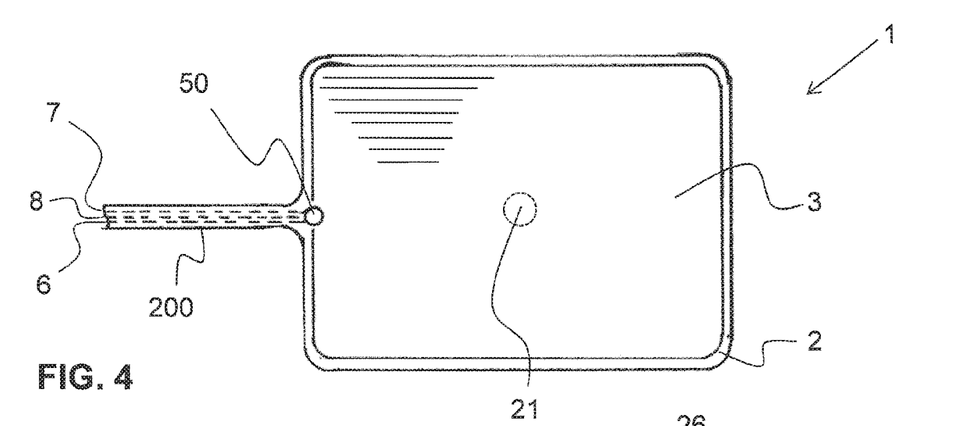
FIG. 4 shows an alternative embodiment of the electrode from FIG. 1.

FIG. 4 shows one alternative embodiment of the electrode from FIG. 1. In contrast to the embodiment from FIG. 1, the first control element 4 is situated directly on the electrode surface 3. Electric lines 6, 7 are routed in the supply line 200 and are connected to the non-illustrated control and power supply unit 900. The second control element 5 can again be situated in the first control element 4, adjacent thereto, or in the control and power supply unit 900.

Further electric lines 8 can likewise lead up to the second electrode support 20. Said electric lines can be measuring lines which are required for measuring the EKG or impedance.

Figure 5:
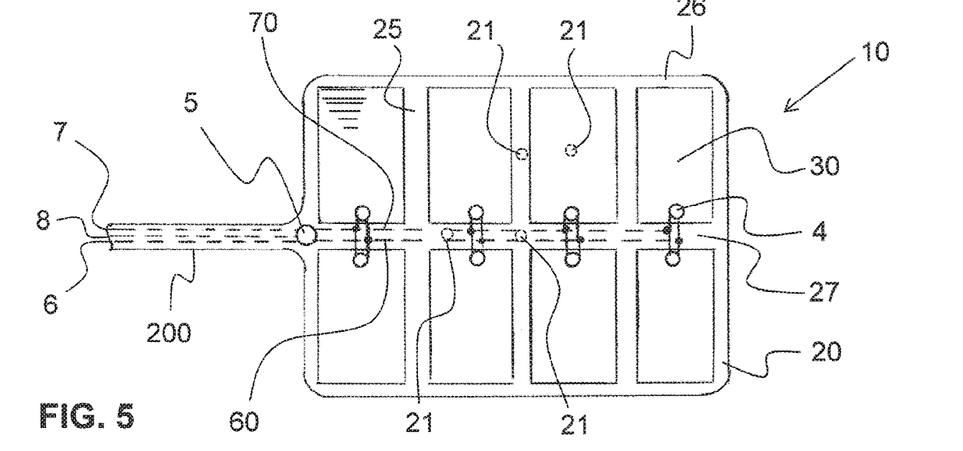
FIG. 5 shows an alternative embodiment of the electrode from FIG. 2.
Figure 6:
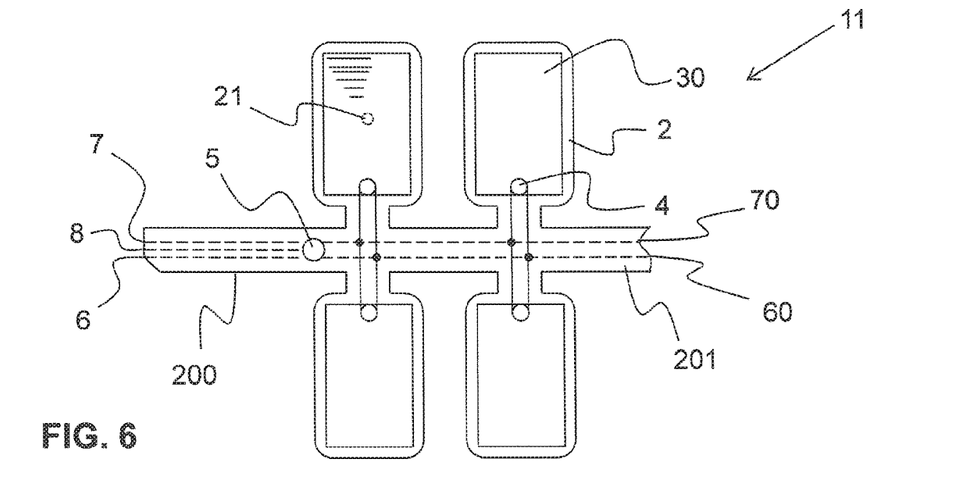
FIG. 6 shows an alternative embodiment of the electrode from FIG. 3.

FIGS. 5 and 6 show one alternative embodiment of the electrode from FIGS. 2 and 3, respectively. In contrast to the embodiment from FIGS. 2 and 3, the first control element 4 is situated directly on the electrode surfaces 30. The first control elements 4 of the electrode surfaces 30 are connected to one another and to the second control element 5 by way of electric lines 60, 70.

The electrode surfaces 3 of the electrodes 1, 10, 11 depicted in FIGS. 4 to 6 are thin, conductive, biocompatible metal foils having low polarization, being made, for example, of platinum or platinum iridium. Alternatively, knitted fabrics or woven fabrics made of thin metal wires can be used instead of the metal foils.

Figure 7:
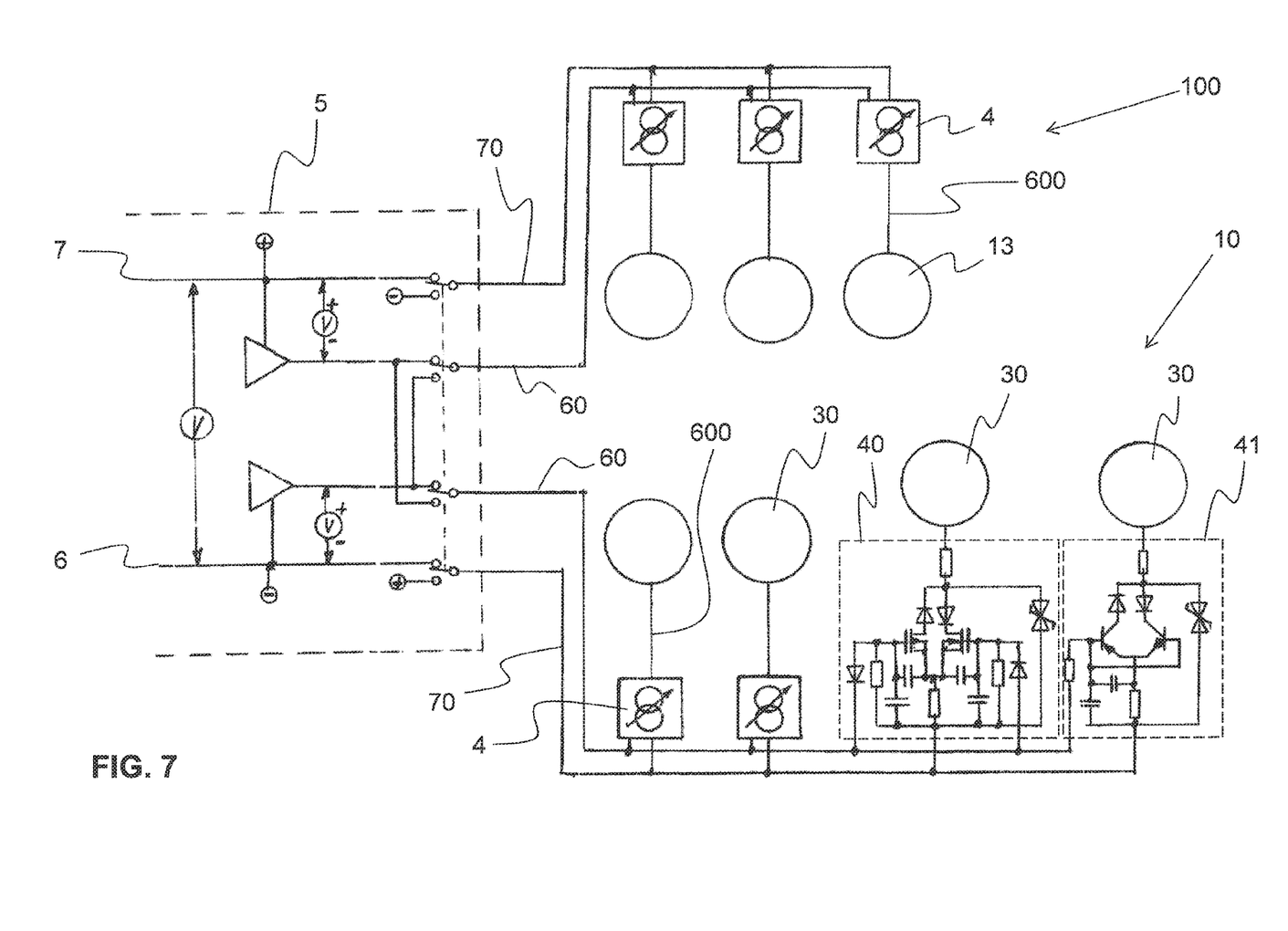
FIG. 7 shows a schematic diagram of the control circuit.
Figure 10:
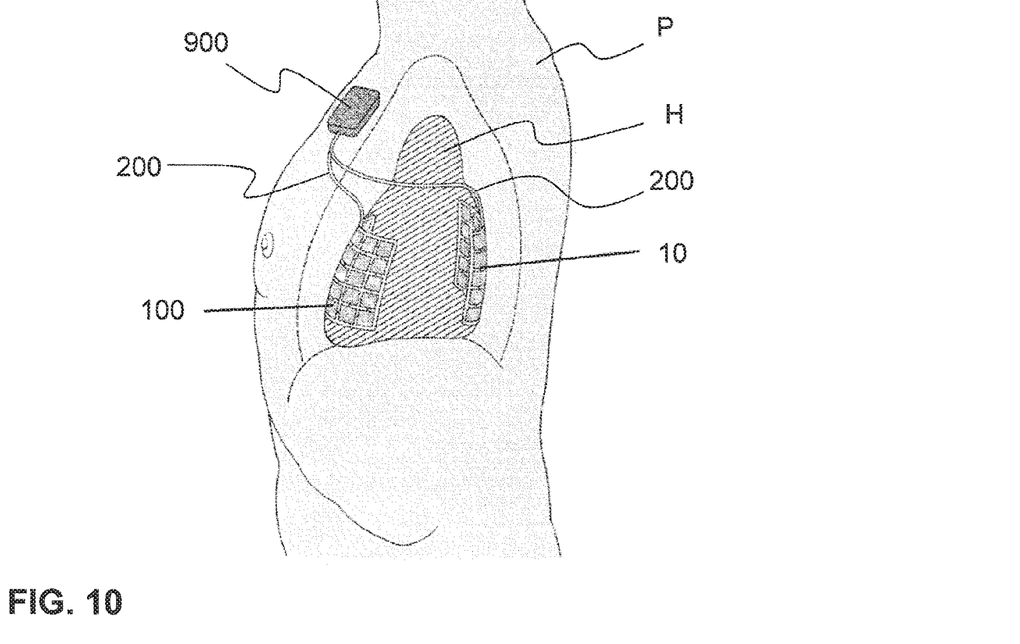
FIG. 10 shows an electrode according to the invention during use.

FIG. 7 shows a schematic diagram of the control circuit of an electrode arrangement according to the invention comprising an electrode 10 and a counterelectrode 100 of the type in use in FIG. 10. The control circuit comprises, for each electrode surface 30, a first control element 4 in the form of a constant-current source, and comprises a second control element 5 which establishes the polarity of the first control elements 4.

The first control element 4 is preferably a transistor-based control element, for example, a first control element 4 having a MOSFET transistor 9 or an alternative first control element 4 having a bipolar transistor 90.

Viewing FIG. 2 and FIG. 7 in combination reveals the possibility of providing only the control with the first control elements 4 on the implant, on the patch electrodes, and of moving the second control with the second control elements 5 to another point, as indicated by way of the connection labeled with the reference numbers 60 and 70 which, in the exemplary embodiment according to FIG. 2, establish the connection to the outside, where the control and power supply unit 900 is located, i.e., in deviation from the exemplary embodiment according to FIGS. 5 and 6.

Figure 8:
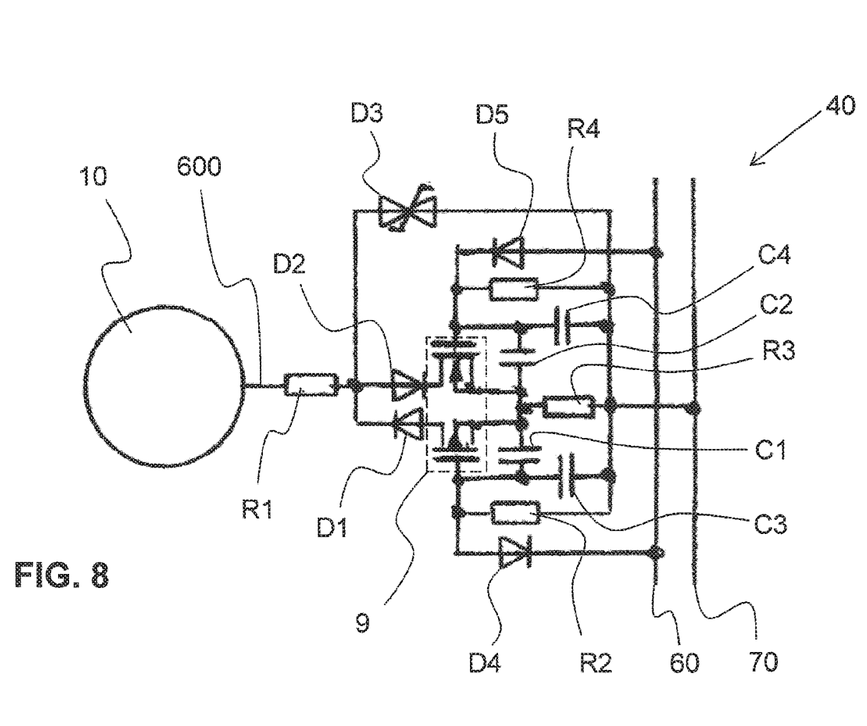
FIG. 8 shows a MOSFET control element.
Figure 9:
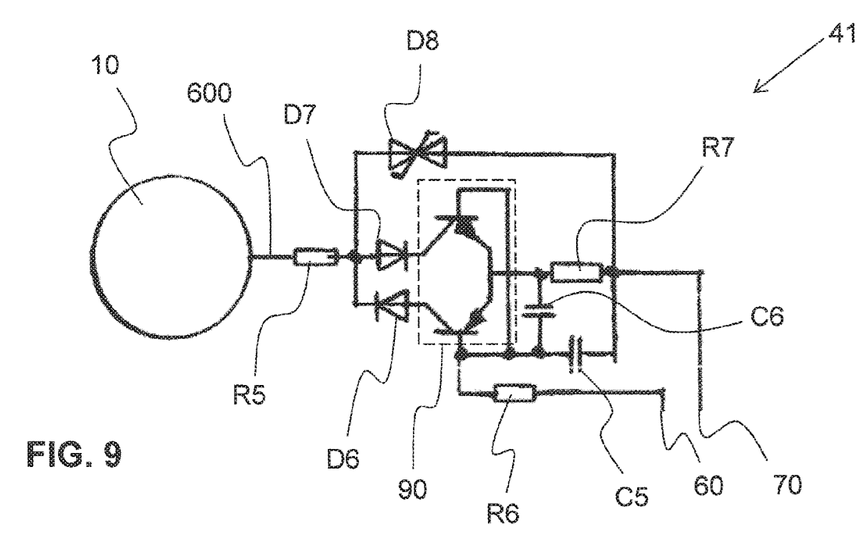
FIG. 9 shows a bipolar control element.

FIG. 8 shows a schematic illustration of a MOSFET control element 40 comprising a MOSFET transistor 9, and FIG. 9 shows a schematic illustration of a bipolar control element 41 having a bipolar transistor 90.

The bipolar control element 41 is described in greater detail in the following with reference to FIG. 9. The principle of current regulation for a current direction (predefined polarity) can be implemented by means of a bipolar transistor 90, an emitter resistor R7, and a reference voltage at the base of the transistor. The emitter resistor R7 is situated at the reference potential (at the positive or negative supply voltage for the current regulator). The collector output is connected to the electrode 10 which rests flat on the heart muscle.

As depicted in FIG. 10, the current circuit is closed via the second counterelectrode 100 lying on the opposite side of the heart. The opposite electrode is likewise provided with current regulators, in order to ensure a defined distribution of the current.

Alternatively, the current circuit can be closed via the control and power supply unit 900. In this case, only one electrode 10 is present, however.

Diodes D6, D7 in the collector lines provide for the intended current direction, for example, of the PNP and NPN transistors. Independently of the intended current direction, the diodes perform a protection function, in order to prevent a control of the bipolar transistors 90 along the collector-base path.

Safety considerations (limitations of high frequencies) are the reason for dispensing with a Miller capacitor (negative feedback capacitor between the collector and the base), in order to prevent feedback from the electrode via the collector onto the base. The limiting of high frequencies is achieved by means of further capacitors.

The voltage drop, measured across the emitter resistor R7, determines the constant current at each individual electrode 1 or each individual electrode segment 10. This voltage can be changed via the control line which leads to the bases of the transistors. As a result, the setpoint current (therapy current), which is supposed to flow through the heart muscle via the corresponding electrode surface, is set.

Each individual transistor automatically regulates itself via its own emitter, as a voltage probe, and thereby maintains the setpoint current which has been set, in the presence of fluctuating transistion resistances, without feedback loops to the control and power supply unit.

The automatic regulating range (change in internal resistance of the transistor) is multiple times larger than the adjustment range via the control voltage.

On the basis of the control voltage between the main line and the base, minus the base emitter voltage $U_{BE}$ of approximately 0.6 volt which drops across the base-emitter path, the constant current can be calculated according to Ohm's law:

$$(U - U_{BE})/R = I$$

wherein $U_{BE} = 0.6$ volt

Since the desired current lies in the µampere range, 0.6 volt should be taken into account, instead of 0.7 volt which is typical.

The emitter resistor R7 should have a size of 20-100 kiloohms, depending on the number of desired electrode segments and the current range which is used.

For medical reasons and due to electrochemical effects, the current direction should be changeable (change the polarity). For this reason, a second transistor (NPN-PNP) having a diode is required in the collector line.

For the particular other current direction, the polarity of the lines to the electrodes can be switched electronically in the control and power supply unit. This applies for the line for the control voltage just as it does for the lines for the therapy current.

In order to switch off the therapy current, the voltage can be lowered to below a threshold of 0.4 volt at at least one of the two control lines. For safety reasons, in addition to lowering the voltage below the aforementioned limit of 0.4 volt, it is provided that the corresponding analog switch is switched to high impedance. For this reason, analog switches having 3 connectors cannot be used.

The resistor R6 has relevance for the case in which the surface element of the electrode has a high resistance to the heart muscle (loss of contact). In this case, the regulating transistor would attempt to draw the missing current across the base. The resistor (R6, approximately 50-150 kiloohms) limits the lost current to tolerable values. In such a configuration, the resistor R6 is connected in series to the resistor R7.

The current loss which sets in can be calculated from the control current minus $U_{BE}$ 0.6 volt divided by (R6+R7).

In normal operation (good contact of the electrode to the heart muscle), the largest portion of the therapy current flows across the collector and only a minimal residual current flows across the base. In the case of amplification factors of 100 to 300, the size of the residual current is only approximately 1 to 0.33 percent of the therapy current.

The resistor R5 [100-500 ohms] has the function of a protective resistor and, together with the diode D8 [two 12-14 volt zener diodes connected back to back], forms a bidirectional overvoltage protection D8. The voltage for the zener diodes is selected to be so high because the zener diodes have a substantially lower leakage current starting at approximately 10-12 volts.

This not only has to do with static discharges which should be dissipated, but also with an effective protection against the defibrillator pulse having an amplitude of up to 1500 volts for 10 milliseconds (25 amperes). Therefore, the resistor must withstand impulse voltages of 1500 volts.

Capacitors C5, C6 are provided for protection against incident high frequency and against the inherent tendency to oscillate. The regulating transistor, by way of its stepless analog regulating task, can find a working point at which it starts to oscillate.

The capacitors are dimensioned in such a way that the correction time does not adversely affect the function. A proven standard value is 100 nanofarads for C6 and 10 nanofarads for C5, if the size of the capacitors does not play a role. In the present application within the electrode, values of 10 nanofarads (dielectric strength 10 volts) for C6 and of 5 nanofarads (voltage strength 20 volts) for C5 are also acceptable. It is permissible for the capacitance to deviate greatly upward in the event of a temperature change, but the indicated capacitance must not be fallen below.

Given a predefined overall surface area F of 6×8 centimeters, an area F of 48 square centimeters results. In the case of a setpoint current density J, for example, of 0.001 milliamperes per square centimeter, a required current I of 0.048 milliamperes results.

For 12 individual surfaces N, for example, wherein each surface has 4 square centimeters, this means that each surface has a maximum current I of 0.004 milliamperes which may be given off, as the maximum, as therapy current.

A value R of 40 kiloohms results for R7. The control voltage is calculated as follows:

$R/N = 3.33$ kiloohms×$I=0.16$ volt=$U$, wherein $R=40$ kiloohms, $N=12$, $I=0.048$ milliamperes $U+u=0.16+0.6=0.76$ volt=$U_{max}$ wherein $u=0.6$ volt (voltage drop)

A maximum control voltage of 0.76 volt must be available in parallel for all 12 current regulators for a multisensor electrode having 12 surfaces.

The setpoint current density can be maintained in an interval of 0.1 to 20 milliamperes per square centimeter, preferably between 1 to 15 microamperes per square centimeter, preferably between 5 and 10 microamperes per square centimeter. Alternatively, the current density J can be maintained around a value contained in the aforementioned intervals. For example, the current density can be maintained around 10 microamperes per square centimeter.

If a MOSFET transistor 9 is used instead of a bipolar transistor 90, as depicted in FIG. 8, the threshold voltage increases relative to the control voltage to approximately 0.8 volt (this is the gate voltage at which MOSFETs just start to conduct), and a voltage drop of 0.25 volt occurs across the Schottky diodes D4, D5 situated in front of the gate. This results in a threshold voltage of 1.05 volts relative to the control line.

The temperature behavior of the diodes counteracts the temperature behavior of the MOSFETs. MOSFETs 9, in contrast to bipolar transistors 90, become higher-impedance when heated.

The primary task of the diodes D4, D5 is to prevent a discharge current across the internal protective diodes of the MOSFETs. Only 2 diodes are required for all current regulators. The gates of the P-channel MOSFETs can also be connected directly in parallel, as is the case with all N-channel MOSFETs.

The resistors R2, R4 (1 megaohm each) are high-impedance and are intended to ensure a reliable blockage of the MOSFETs. This is necessary due to the diodes. Two resistors are sufficient for all individual areas of the multi-area electrode.

The capacitors C3, C4, as is also the case with the capacitors C1, C2, are provided as protection against incident high frequency and against the tendency to oscillate (no difference from the circuit having the bipolar transistors). In this case as well, two capacitors C3, C4 suffice for all individual surfaces. While C3 and C4 are sufficient for all current regulators, the capacitors C1 and C2 should be provided in each current-regulating circuit.

FIG. 10 shows an electrode 10 according to the invention in use, wherein said electrode is situated on a first outer surface of the heart H of a patient P, and a counterelectrode 100 is situated on a second outer surface of the heart H, which is essentially opposite the first side. Preferably, the electrode 10, essentially, and the counterelectrode 100 are situated on a front and a rear surface, respectively, of the heart. Alternatively, the electrodes can also be situated on a left- or right-oriented surface of the heart. The advantage of these arrangements is that the current flows substantially through the heart or through the heart muscle.

The counterelectrode 100 can be designed identical to or substantially identical to the opposite electrode 10. Said electrode can also have a different distribution or segmentation of the electrode surfaces.

Supply lines 200 extend from the electrodes 10, from each electrode 10, 100 to a shared control and power supply unit 900 which, for example, comprises a generator and receiving unit, a telemetry unit, and a power supply unit.

An electrode according to the invention makes it possible to improve the effect of the treatment while simultaneously increasing the safety of the treatment.

LIST OF REFERENCE NUMBERS 1 individual electrode
10 segmented electrode
100 counterelectrode
11 alternative segmented electrode
2 first electrode support
20 second electrode support
200 supply line
201 connection strand
21 one-way valve 22 opening
23 diaphragm
25 web
26 border
27 central web
3 first electrode surface
30 second electrode surface
4 first control element
40 MOSFET control element
400 control module
41 bipolar control element
5 second control element
6-8 electric line
9 MOSFET transistor
90 bipolar transistor
900 control and power supply unit
R1-R7 resistor
D1-D8 diode
C1-C6 capacitor
I current
J current density
U voltage
P patient
H heart

The invention claimed is:

1. An electrode system for treating organic tissue by means of direct current, comprising:
 an electrode support,
 two or more electrically separated electrodes, each having an electrically conductive electrode flat surface which is separately embedded in the electrode support,
 two or more first control elements, each associated with a respective one of said two or more electrically separated electrodes,
 a second control element, and
 a control and power supply unit, and
 wherein each of the electrically separated electrodes is connected to the associated first control element by electric lines,
 wherein the second control element is configured in such a way that each individual electrically separated electrode is controllable by the associated first control element in such a way that a current density provided within a predetermined interval for each electrode surface of each electrically separated electrode is maintained, and
 wherein the second control element is situated at a distance from the electrically separated electrodes, in the control and power supply unit.

2. The electrode system as claimed in claim 1, wherein each first control element is situated on a back or at a side of the associated electrically separated electrode.

3. The electrode system as claimed in claim 1, wherein the electrode support is a shared, contiguous, integrally formed electrode support for embedding the surfaces of the two or more electrically separated electrodes.

4. The electrode system as claimed in claim 1, wherein the electrode support comprises at least a first and a second electrode support, wherein at least two of the electrically separated electrodes are embedded in a respective one of the electrode supports surrounding the particular separated electrode, and the first electrode support and the second electrode support are interconnected by way of a connection strand.

5. The electrode system as claimed in claim 1, wherein the first control element comprises a MOSFET or a bipolar transistor.

6. The electrode as claimed in claim 1, further comprising one or more one-way valves within the electrode support, wherein the electrode support has an organ oriented side and a far side, wherein the one or more one-way valves are provided between the organ oriented side and the far side, permitting drainage of fluid which has accumulated under the electrode surfaces.

7. The electrode system as claimed in claim 6, wherein the one or more one-way valve is situated within any one of the electrically separated electrode surfaces.

8. The electrode system as claimed in claim 6, wherein the one or more one-way valve is situated between adjacent electrically separated electrode surfaces.

9. The electrode system as claimed in claim 6, wherein the one or more one-way valve is a diaphragm valve.

10. An electrode system for treating organic tissue by means of direct current, comprising:
 an electrode support,
 two or more electrically separated electrodes, each having an electrically conductive electrode flat surface which is separately embedded in the electrode support,
 two or more first control elements, each associated with a respective one of said two or more electrically separated electrodes,
 a second control element,
 a control and power supply unit, and
 at least one electric line connecting the second control element to the control and power supply unit,
 wherein each of the electrically separated electrodes is connected to the associated first control element by further electric lines,
 wherein the second control element is configured in such a way that each individual electrically separated electrode is controllable by the associated first control element in such a way that a current density of the surface for each one of the at least one electrically separated electrodes is maintained around a predetermined value, and
 wherein the second control element is situated at a distance from the electrically separated electrodes in a connection area of the electrically separated electrodes.

11. The electrode system as claimed in claim 10, wherein the electrode support is a shared, contiguous, integrally formed electrode support for embedding two or more of the electrically separated electrode surfaces.

12. The electrode system as claimed in claim 10, further comprising one or more one-way valves within the electrode support,
 wherein the electrode support has an organ oriented side and a far side, and
 wherein the one or more one-way valves are provided between the organ oriented side and the far side permitting the drainage of fluid which has accumulated under the electrode surfaces.

13. The electrode system as claimed in claim 10, wherein the electrode support comprises at least a first and a second electrode support, wherein at least two of the electrically separated electrode surfaces are embedded in a respective one of the electrode supports surrounding the particular electrode surfaces, and the first electrode support and the second electrode support are interconnected by way of a connection strand.

14. A method for controlling the current density on an electrode of an electrode system for treating organic tissue by means of direct current, the electrode system comprising an electrode support, two or more electrically separated electrodes, each having an electrically conductive electrode flat surface which is separately embedded in the electrode support, two or more first control elements associated with a respective one of the two or more electrically separated electrodes, a second control element, a control and power supply unit, and at least one electric line connecting the second control element to the control and power supply unit, wherein each of the electrically separated electrodes is connected to the associated first control element by further electric lines, wherein the second control element is situated at a distance from the electrically separated electrodes in a connection area of the electrically separated electrodes, the method comprising:

configuring the second control element in such a way that current flowing through each of the individual electrically separated segmented electrodes is regulated in such a way either that a current density provided within a predetermined interval for each individual electrode surface is maintained or that a current density for each of the at least one electrode surface is maintained around a predetermined value.

15. The method for controlling the current density on an electrode as claimed in claim 14, wherein the electrically separated electrode of the electrode system can be used as a current-supplying electrode or a current-receiving electrode.

16. An electrode system for treating organic tissue by means of direct current, comprising:

an electrode support, two or more electrically separated electrodes, each having an electrically conductive electrode flat surface which is separately embedded in the electrode support, two or more first control elements, each associated with a respective one of said two or more electrically separated electrodes, a second control element, a control and power supply unit, and at least one electric line connecting the second control element to the control and power supply unit, wherein each of the electrically separated electrodes is connected to the associated first control element by further electric lines, wherein the second control element is configured in such a way that each individual electrically separated electrode is controllable by the associated first control element in such a way that a current density provided within a predetermined interval for each electrode surface of each electrically separated electrode is maintained, and wherein the second control element is situated at a distance from the electrically separated electrodes in a connection area of the electrically separated electrodes.

\* \* \* \* \*